United States Patent
Young et al.

(10) Patent No.: US 11,517,277 B2
(45) Date of Patent: Dec. 6, 2022

(54) VISUALIZING COLLIMATION ERRORS

(71) Applicant: KONINKLIJKE PHILIPS N.V., Eindhoven (NL)

(72) Inventors: Stewart Young, Hamburg (DE); Daniel Bystrov, Hamburg (DE); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 539 days.

(21) Appl. No.: 16/468,994

(22) PCT Filed: Dec. 14, 2017

(86) PCT No.: PCT/EP2017/082928
§ 371 (c)(1),
(2) Date: Jun. 12, 2019

(87) PCT Pub. No.: WO2018/109127
PCT Pub. Date: Jun. 21, 2018

(65) Prior Publication Data
US 2021/0401391 A1     Dec. 30, 2021

(30) Foreign Application Priority Data
Dec. 15, 2016 (EP) .................................. 16204212

(51) Int. Cl.
*G01N 23/04* (2018.01)
*A61B 6/00* (2006.01)
(Continued)

(52) U.S. Cl.
CPC ............. *A61B 6/463* (2013.01); *A61B 6/06* (2013.01); *A61B 6/08* (2013.01); *A61B 6/488* (2013.01);
(Continued)

(58) Field of Classification Search
CPC .. A61B 6/06; A61B 6/08; A61B 6/488; A61B 6/542; A61B 6/50; A61B 6/5241;
(Continued)

(56) References Cited

U.S. PATENT DOCUMENTS

| | | | | |
|---|---|---|---|---|
| 5,570,430 A | * | 10/1996 | Sheehan | ............... G06T 7/0012 378/98.5 |
| 6,026,142 A | * | 2/2000 | Gueziec | .................... G06T 7/12 378/4 |

(Continued)

OTHER PUBLICATIONS

PCT International Search Report, International application No. PCT/EP2017/082928, dated Apr. 3, 2018.

(Continued)

*Primary Examiner* — Irakli Kiknadze
(74) *Attorney, Agent, or Firm* — Larry Liberchuk

(57) ABSTRACT

The field of view of an X-ray imaging system should be set appropriately to ensure that anatomical information of interest is not omitted. In particular, it is necessary to ensure that the operator of an X-ray system does not allow a patient to leave the X-ray imaging system until it is certain that the correct anatomy has been imaged. This application discusses a technique enable the visualization of a field of view boundary error caused by the incorrect configuration of an X-ray imaging system. Optionally, the boundary error is displayed either on a user display of a system console, or by projecting the field of view error onto the patient in the X-ray system. Thus, an operator of the system may be alerted to the presence of a boundary error, enabling a new X-ray exposure to be taken, if necessary.

13 Claims, 6 Drawing Sheets

(51) Int. Cl.
| | |
|---|---|
| *G06T 7/11* | (2017.01) |
| *G06V 10/25* | (2022.01) |
| *A61B 6/06* | (2006.01) |
| *A61B 6/08* | (2006.01) |
| *G06T 7/00* | (2017.01) |

(52) U.S. Cl.
CPC .......... *A61B 6/5258* (2013.01); *G06T 7/0012* (2013.01); *G06T 7/11* (2017.01); *G06V 10/25* (2022.01); *G06T 2200/24* (2013.01); *G06T 2207/10116* (2013.01); *G06T 2207/20076* (2013.01); *G06T 2207/30004* (2013.01); *G06V 2201/03* (2022.01)

(58) Field of Classification Search
CPC ......... A61B 6/545; A61B 6/544; A61B 6/032; A61B 6/4452; A61B 6/583; A61B 6/588; A61B 6/405; A61B 6/4241; A61B 6/4291; A61B 6/482; A61B 6/5282; A61B 6/4085; A61B 6/4266; A61B 6/503; A61B 6/5217; A61B 8/5207; A61B 6/463; A61B 6/465; A61B 6/466; A61B 6/14; A61B 6/587; A61B 6/5258; A61B 2034/105; A61B 34/10; A61B 5/055; A61B 5/0263; A61B 6/507; A61B 5/364; A61B 5/346; A61B 5/319; A61B 5/026; A61B 5/02007; A61B 5/349; A61B 6/501; A61B 5/1075; A61B 5/107; A61B 5/0044; G06T 2207/10116; G06T 2207/30168; G06T 7/0012; G06T 2207/20221; G06T 2207/30061; G06T 7/0014; G06T 2207/10144; G06T 2207/20021; G06T 2207/20104; G06T 2207/30004; G06T 7/11; G06T 7/10; G06T 2207/20076; G06T 2207/20081; G06T 2207/20084; G06T 2223/419; G06T 2223/612; G06T 1/249; G06T 2207/30101; G06T 2207/10072; G06T 2207/30048; G06T 7/12; G06T 7/149; G06T 2200/24; G06T 2207/10132; G06T 7/60; G06T 2207/3008; G06T 5/005; G06T 5/50; G06T 7/337; G06T 7/50; G06T 2207/30008; G06T 2207/10076; G06T 2210/41; G06T 2207/10088; G06T 2200/04; G06T 2207/10081; G01N 2223/419; G01N 2223/612; G01N 23/046; G01N 23/04; G01N 2223/304; G01N 2223/306; G01N 2223/401; G01N 2223/646; G01N 23/10; G01N 20/00; G06V 10/25; G06V 2201/03; G16H 50/50; G16H 50/20; G16H 30/40; G16H 50/30; G16H 40/20; G16H 40/63
USPC .................................. 378/62, 108, 205, 206
See application file for complete search history.

(56) References Cited

U.S. PATENT DOCUMENTS

| | | | |
|---|---|---|---|
| 7,490,986 | B2 | 2/2009 | Takekoshi |
| 7,559,693 | B2 | 7/2009 | Sonani |
| 9,155,509 | B2 | 10/2015 | Lalena |
| 9,715,744 | B2 * | 7/2017 | Liu ...................... G06T 11/005 |
| 2003/0165216 | A1 | 9/2003 | Walker |
| 2004/0116804 | A1 * | 6/2004 | Mostafavi ............ A61B 6/5288 600/428 |
| 2007/0268997 | A1 * | 11/2007 | Zhu ...................... A61B 6/5282 378/7 |
| 2012/0039447 | A1 | 2/2012 | Lalena |
| 2014/0126784 | A1 * | 5/2014 | Hsieh .................... G06T 11/005 382/128 |
| 2014/0219524 | A1 * | 8/2014 | Takeguchi ............. G16H 50/30 382/128 |
| 2014/0334708 | A1 * | 11/2014 | Sakata ................... A61B 6/541 382/131 |
| 2014/0348296 | A1 | 11/2014 | Goossen |
| 2015/0228071 | A1 | 8/2015 | Jockel |
| 2015/0245776 | A1 * | 9/2015 | Hirohata ................ A61B 6/037 600/504 |
| 2017/0071479 | A1 * | 3/2017 | Kano ..................... A61B 5/026 |
| 2017/0090571 | A1 * | 3/2017 | Bjaerum ............. A61B 8/4254 |
| 2020/0008768 | A1 | 1/2020 | Young |

OTHER PUBLICATIONS

Taylor, N., "The Art of Rejection: Comparative Analysis Between Computed Radiography and Digital Radiography Workstations in the Accident and Emergency and General Radiology Departments at a District General Hospital Using Customized and Standardized Reject Criteria Over a Three-Year Period", Radiography (2014), Elsevier, p. 1-6.

European Commission. European Guidelines on Quality Criteria for Diagnostic Radiographic Images. 1996.

Vik, T. et al., "A New Method for Robust Organ Positioning in CT Images", 2012 9th IEEE International Symposium on Biomedical Imaging (ISBI), p. 338, May 2012.

* cited by examiner

VISUALIZING COLLIMATION ERRORS

FIELD OF THE INVENTION

This invention relates generally to user-feedback in X-ray imaging systems, and more particularly to a display unit for an X-ray system, an X-ray imaging system incorporating the display unit, a method for identifying a boundary error in X-ray image data, a computer program element, and a computer readable medium.

BACKGROUND OF THE INVENTION

Setting the field of view (FOV) for radiographic exposures is a complex task which requires the attention of a trained radiographer. Mistakes made when setting the field of view, for example collimation errors, can cause the extremes of organs to be omitted from X-ray image data, even when it is desired that such organs are included in the X-ray data. Such a situation will require the X-ray image to be retaken. Often, in such a situation the patient must be recalled to the hospital where the imaging took place to enable another exposure to be made.

The article by Taylor, N, entitled "The art of rejection: Comparative analysis between Computed Radiography and Digital Radiography workstations in the Accident and Emergency and General radiology departments at a district general hospital using customized and standardized reject criteria over a three-year period", Radiography (2014), Elsevier, http://dx.doi.org/10.1016/j.radi.2014.12.003 discusses the problems of faulty radiographic exposures.

SUMMARY OF THE INVENTION

According to a first aspect, there is provided a display unit for an X-ray system. The display unit comprises:
 a data communication interface;
 a processing unit; and
 a display output unit comprising a projection unit.

The data communication interface is configured to obtain first X-ray image data of a first portion of a region of interest of an object using an X-ray imager, wherein the first X-ray image data is obtained using an X-ray imager having an adjustable field of view set to an initial field of view state.

The processing unit is configured to analyse the first X-ray image data to identify a boundary error in the first X-ray image data, to define a boundary error region contiguous to the first X-ray image data based on the analysis of the first X-ray image data; and to generate a boundary error indication based on the defined boundary error region.

The display output unit is configured to display the boundary error indication to a user by projecting the boundary error indication onto a second portion of the region of interest of the object using the projection unit.

Therefore, it is possible to directly illustrate to a user of an X-ray imager the fact that a further X-ray exposure will be required owing to an insufficient image quality. The omitted area can be displayed to the user, to facilitate re-setting of the device.

According to an example, there is provided a display unit for an X-ray system. The display unit comprises:
 a data communication interface;
 a processing unit; and
 a display output unit.

The data communication interface is configured to obtain first X-ray image data of a first portion of a region of interest of an object using an X-ray imager, wherein the first X-ray image data is obtained using an X-ray imager having an adjustable field of view set to an initial field of view state.

The processing unit is configured to analyse the first X-ray image data to identify a boundary error in the first X-ray image data, to define a boundary error region contiguous to the first X-ray image data based on the analysis of the first X-ray image data; and to generate a boundary error indication based on the defined boundary error region.

The display output unit is configured to display the boundary error indication to a user.

Optionally, the display output unit further comprises:
 a user interface display unit. The user interface display unit is further configured to display the boundary error indication on the user interface display unit.

Therefore, the boundary error region can be clearly displayed to a user on a screen of a digital X-ray machine, for example.

Optionally, the processing unit is further configured to combine the boundary error indication with the first X-ray image data to form annotated first X-ray image data, and the display output unit is further configured to display the boundary error indication to a user by displaying the annotated first X-ray image data on the user interface display unit.

Therefore, the annotated X-ray image data may be exported, to enable users of the annotated X-ray image data who are not physically located at the X-ray imager to identify a boundary error.

Optionally, the display unit further comprises:
 a projection unit.
The display output unit is further configured to project the boundary error indication onto a second portion of the region of interest of the object using the projection unit.

Therefore, a boundary error region may be directly projected onto the region of interest of the patient in a way that is difficult for a system user to overlook. This reduces the likelihood that a user would leave the X-ray room before corrective action (such as the taking of a new X-ray image) is taken.

Optionally, the processing unit is further configured to calculate an updated field of view state, and to display the updated field of view indication by (i) projecting the updated field of view indication onto a third portion of the region of interest of the object, and/or (ii) displaying the updated field of view indication on the user interface display unit.

Optionally, the projection unit comprises a digital projection unit. The boundary error indication is projected onto a second portion of the region of interest of the object using a digital projection unit.

A digital projection unit may provide indications of boundary error regions having many different shapes.

Optionally, the projection unit further comprises:
 a light filter element operatively coupled to the processing unit and configurable to extend at least partially over the periphery of a light path of a light source directed at the region of interest.

The processing unit is further configured to configure the light filter element to extend at least partially over the periphery of the light path of the light source located inside the X-ray source based on the boundary error indication, and to send an illumination signal to illuminate a light source inside the X-ray source.

Therefore, the existing light illumination mechanism of many X-ray machines may be adapted to highlight peripheral errors in the setting of the field of view.

Optionally, the boundary error indication and/or the updated field of view indication is displayed on the user interface and/or on a portion of the region of interest of the object using one or more of (i) a coloured rectangular indication, (ii) a region having lower or higher brightness compared to the first and/or second X-ray image data, (iii) a flashing indication, (iv) an outline of an anatomical feature optionally comprising an indication of a cut-off region.

Optionally, the processing unit is configured to analyse the first X-ray image data by comparing a portion of the first X-ray image data to an anatomical model and/or a probabilistic anatomical atlas.

According to a second aspect, there is provided an X-ray imaging system comprising:
an X-ray source;
an X-ray detector; and
a display unit according to the first aspect or its optional embodiments.

The X-ray source is configured in an initial field of view state to illuminate a region of interest of an object with X-ray radiation, and the X-ray detector is configured to receive first X-ray image data of a first portion of the region of interest of an object.

The display unit is configured to display a boundary error indication of the first X-ray image data to a user.

According to a third aspect, a method for identifying a boundary error in X-ray image data is provided. The method comprises:
a) obtaining first X-ray image data of a first portion of a region of interest of an object using an X-ray imager, wherein the first X-ray image data is obtained using an X-ray imager having an adjustable field of view set to an initial field of view state;
b) analysing the first X-ray image data to identify a boundary error in the first X-ray image data;
c) defining a boundary error region contiguous to the first X-ray image data based on the analysis of the first X-ray image data;
d) generating a boundary error indication based on the boundary error region; and
e) displaying to a user the boundary error indication;
wherein displaying the boundary error indication to a user further comprises:
e4) projecting the boundary error indication onto a second portion of the region of interest.

Optionally, displaying the boundary error indication to a user further comprises:
e1) displaying the boundary error indication on a user interface display of an X-ray imaging system.

According to an example, there is provided a method for identifying a boundary error in X-ray image data, comprising:
a) obtaining first X-ray image data of a first portion of a region of interest of an object using an X-ray imager, wherein the first X-ray image data is obtained using an X-ray imager having an adjustable field of view set to an initial field of view state;
b) analysing the first X-ray image data to identify a boundary error in the first X-ray image data;
c) defining a boundary error region contiguous to the first X-ray image data based on the analysis of the first X-ray image data;
d) generating a boundary error indication based on the boundary error region; and
e) displaying to a user the boundary error indication.

According to a fourth aspect, there is provided a computer program element for controlling a processing unit and/or system as claimed in the first aspect, which, when the computer program element is executed by the processor and/or system, is adapted to perform the method of the third aspect.

According to a fifth aspect, there is provided a computer readable medium having stored the computer program element of the fourth aspect.

In the following specification, the term "X-ray image data" refers to a data structure containing an array of pixels, wherein each pixel represents the intensity of a received X-ray at a specific pixel following the traversal of that X-ray through a region of interest of a patient. When assembled into a two-dimensional image, the intensity values provide an additive image representing the integral of the X-ray absorption at each pixel location.

In the following specification, the term "X-ray source" refers to an X-ray source containing, for example, a rotating anode X-ray tube. This emits X-ray radiation towards a region of interest of a patient to be imaged. The X-ray radiation traverses the patient at the region of interest, and is received by an X-ray detector, which may also be considered to be part of an X-ray imaging system. The X-ray imager may comprise automatically settable field of view parameters, such as, for example, an adjustable collimator arrangement, adjustable pan or tilt servomotors, adjustable height or x-y coordinate setting. In addition, the X-ray detector may be translated vertically or horizontally.

In the following specification, the term "field of view" refers to a portion of the region of interest that an X-ray imager may capture during a typical exposure. The field of view is generically defined by the distance of an X-ray imager from the X-ray detector and/or patient, and the size of the X-ray detector's aperture. The field of view may be translated across the region of interest by moving the X-ray imager in an x-z plane. The field of view may also be changed by panning or tilting the X-ray imager. The field of view may be cropped or enlarged by adjusting a collimator shutter, or shutters, of an X-ray source. Therefore, it will be appreciated that there are many ways to adjust the field of view of an X-ray imager.

In the following specification, the term "anatomical model" refers to a data structure, typically stored and executed on a processing means such as a computer. The anatomical model contains information defining the location and shape of common anatomical features of patients. A typical anatomical model defines a section of a generic patient body. The anatomical model contains a representation of structures such as lungs, rib bones, a spine, for example, and the likelihood that a certain anatomical element is present in a certain position. The anatomical model may be designed to allow anatomical elements to be identified from incomplete portions of an image of an organ.

The term "boundary error region" defines an unanatomical region in the X-ray image data. It will be appreciated that in this case of an incorrect collimation of the field of view, the boundary error region will appear to be cropped. For example, the extreme left or extreme right hand portions of a lung lobe may be missing from the X-ray image data. However, in this case of a field of view which is incorrectly set owing to a poor pan or tilt setting, a boundary error region may be defined by an anatomical element which is present, but warped, for example, into a "keystone shape". In other words, a boundary error region of the X-ray image data defines an area of the image which is not a faithful, or accurate reproduction of the anatomy of the patient.

The term "boundary error indication" defines an indication which enables a medical professional to be alerted to the location of a boundary error region on a patient after a first X-ray exposure has been performed. One way of achieving this is to highlight the presence of the boundary error by altering an attribute of the displayed X-ray image data. For example, the boundary error region could be surrounded with a rectangle, or shaded a different colour on a user interface screen. Alternatively, the boundary error region could be directly projected onto the region of interest of a patient.

Thus, it is a basic idea of the present specification to directly highlight the location of a problematic region arising from incorrect setting of the field of view quickly after a first X-ray exposure has been made. This firstly highlights to a user of an X-ray imager that there is a field of view error, and secondly can provide them with feedback to enable the field of view of the X-ray imager to be re-set quickly.

Although this application discusses the concept in terms of lung imaging based on the posterior-anterior view, it will be appreciated that the techniques discussed herein have wide applicability in radiography, wherever an initial X-ray image has missing boundary elements.

BRIEF DESCRIPTION OF THE DRAWINGS

Exemplary embodiments will be described with reference to the following drawings.

DETAILED DESCRIPTION OF EMBODIMENTS

Chest radiography is the most commonly performed clinical imaging examination, and plays an important role in detecting and diagnosing many diseases of the thoracic anatomy. The image quality of the acquired X-ray image data is dependent on a wide range of factors, such as the inclusion of appropriate anatomy within the field of view (FOV), the contrast of structures of interest in the FOV, and the positioning of a patient's thorax with respect to the X-ray imaging equipment.

The task of setting the field of view (FOV) for an exposure in a digital X-ray system is conventionally performed by a radiographer. The patient is initially positioned in a region of interest in front of an X-ray detector. Then, visible light, shining from within the tube-head of the X-ray equipment, and matching to the field of the X-ray radiation pattern, is used to project the field of view onto a patient's body. The height of the tube-head may firstly be varied, and then the height of a "bucky" containing the detector, and finally an adjustment may be made to the collimator opening, for example.

Figure 1:
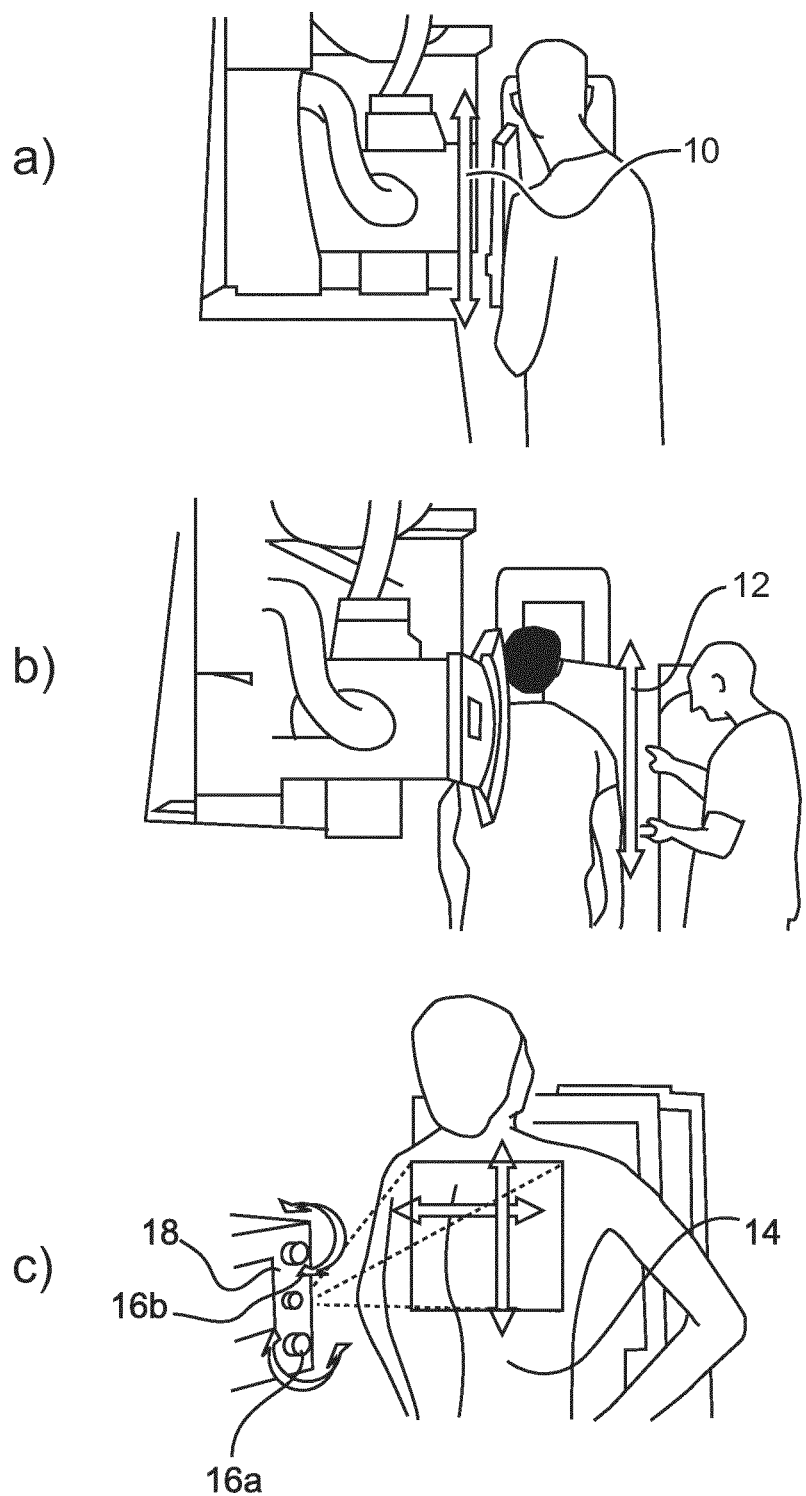
FIGS. 1a) to 1c) illustrate stages in configuring an initial field of view during an X-ray exposure.

FIG. 1 shows a patient being examined in one of the most common projection geometries in clinical radiography, the posterior-anterior view of the chest. In FIG. 1, the X-ray source has been positioned such that the X-ray beams enter through the posterior of the chest, and exit the anterior of the chest, before reaching the X-ray detector.

FIG. 1a) shows an operator adjusting the height 10 of the X-ray source. FIG. 1b) shows the operator adjusting the height 12 of the "bucky" containing the X-ray detector. FIG. 1c) shows the projection of a visible light collimation pattern 14 representing the field of view at a certain collimation state. The collimation pattern corresponds to the pattern of X-ray exposure when the X-ray exposure is in progress. Typically, the collimation pattern 14 is refined using controls 16a, 16b on an item of X-ray source control equipment 18. Varying the collimation pattern enlarges or shrinks the field of view of the system.

In clinical routine, aspects which determine the image quality are dependent to an extent upon the system operator's skill. Although standard operating procedures may be established by medical institutions, with an aim of ensuring a predefined minimum quality standard, enabling the minimization of common sources of potential error, opportunities for causing field of view errors still present themselves.

Setting the field of view of the X-ray equipment is an important part of an operator's task, but it is also a task which is prone to error. A common situation is "cut-off". This refers to an error in the setting of the field of view, whereby part of the anatomy of interest is, accidentally, not included within the X-ray image. Cut-off is one of the most common errors, and typically requires a retake of an entire X-ray image.

Ordinarily, to obtain the full posterior-anterior lung image, cut-off exposures would need to be discarded. A completely new exposure would have to be made in each case. This is wasteful of X-ray facility time, and results in a patient receiving at least two times the required dose, compared to a case where the image had been taken correctly in one take. Thus, an approach for reducing such extra doses in response to field of view errors is required.

Figure 2:
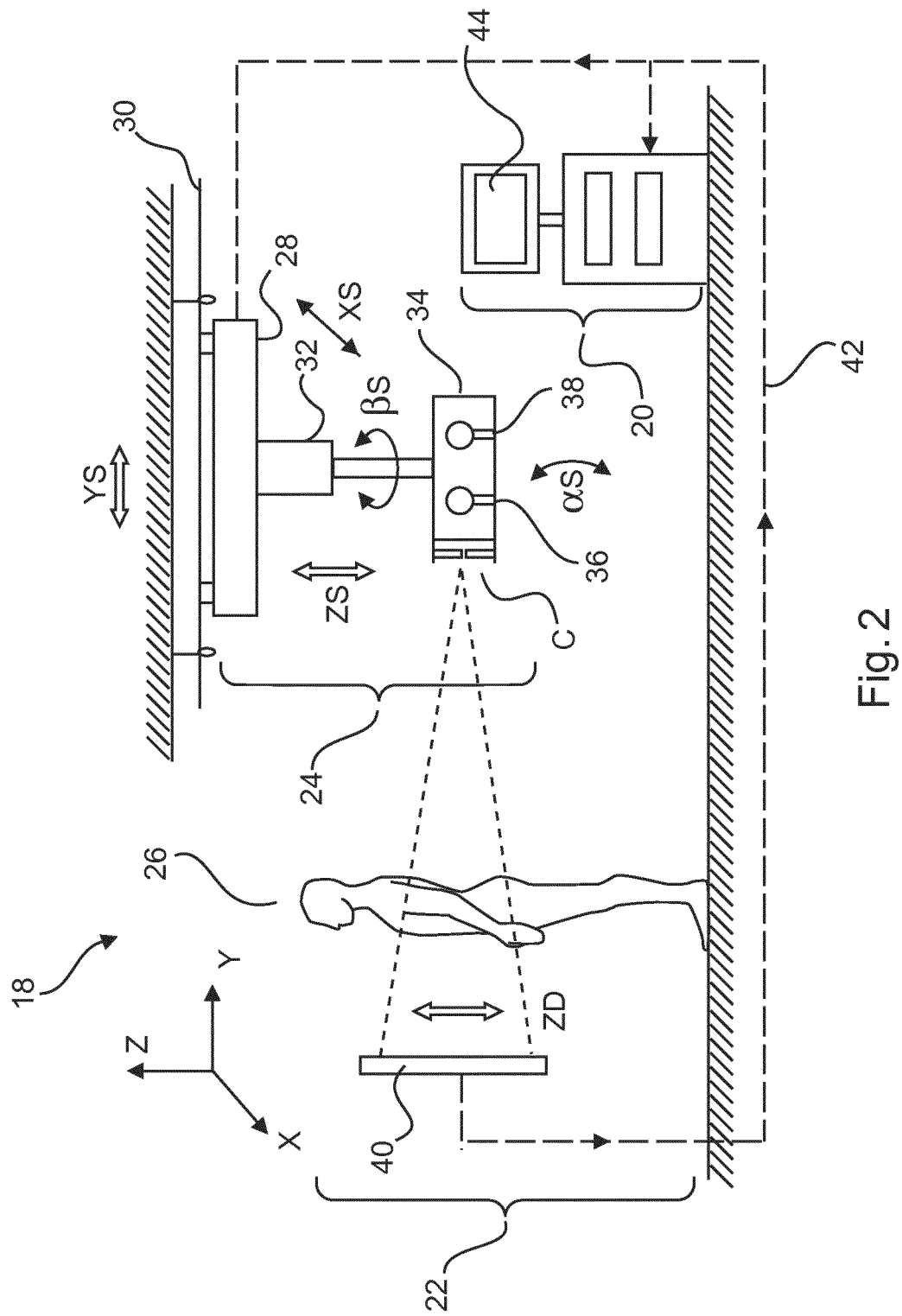
FIG. 2 illustrates an X-ray system.

FIG. 2 shows an X-ray imaging system 18. The X-ray imaging system comprises a control apparatus 20, a detection assembly 22, and an X-ray imaging source assembly 24. A patient typically stands in the region of interest 26 in-between the X-ray source assembly 24 and the detection assembly 22.

FIG. 2 illustrates a patient in the posterior-anterior position. The X-ray imaging source assembly 24 comprises a roof-mounted dolly 28 configured to be suspended from a ceiling rail 30 of an X-ray imaging suite.

The X-ray imaging source assembly 24 is typically supported on the ceiling rail 30, enabling translational movement of the X-ray source towards or away from the patient (YS). The X-ray imaging source is suspended from the rail by a support member 32 which is movable in an up-down direction (towards and away from the floor, ZS axis), and also rotatable around the axis of the support member (βS).

An X-ray imaging source assembly 34 is suspended from the support member 32 and comprises an enclosure containing an X-ray source 36 configured to emit X-ray radiation towards the region of interest 26, and a visible light source 38 configured to emit visible light towards the region of interest 26.

The X-ray source 36 is, for example, a rotating anode X-ray tube. The visible light source 38 is typically provided as an incandescent or an LED light. A collimation element C is located in-between the region of interest 26 and the X-ray source 36 and the visible light source 48.

The collimation element C is configured to shape the outer edges of the X-ray beam. A simple collimator comprises a shutter arranged to cover the aperture of the X-ray imager progressively. More sophisticated collimation elements comprise two shutters arranged in an orthogonal planar relationship to each other, enabling the size of the field of view to be altered. More complicated collimation arrangements include three-sided, four-sided, or "iris" collimator shutter arrangements.

Therefore, the collimation element C facilitates the definition of the outer extent of the field of view both of the X-ray radiation pattern and the visible light radiation pattern. It is noted also that the X-ray imaging source is tiltable by an angle αS. The entire X-ray imaging arrangement may also be translated laterally (in FIG. 3, in a direction into, or out of, the page) through the XS dimension as shown on the drawing.

Figure 3:
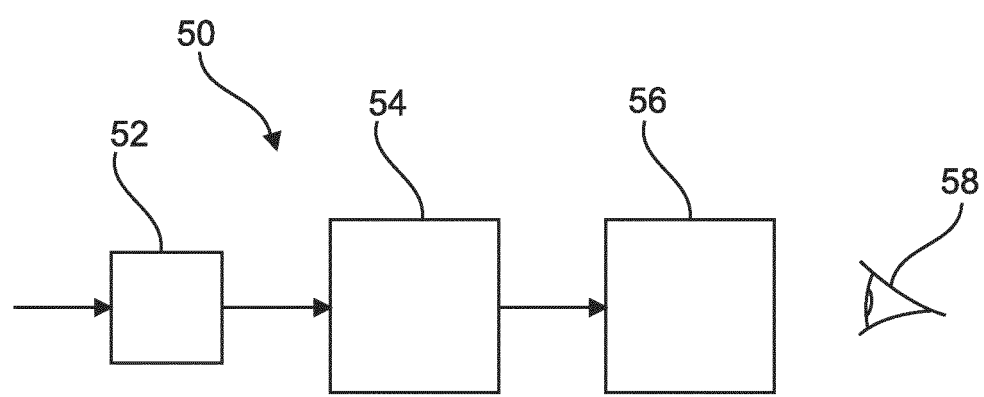
FIG. 3 illustrates a display unit according to a first aspect.

Thus, in the X-ray imaging system illustrated in FIG. 3, the field of view of the region of interest may be adjusted by manipulating the collimator element or elements C. It is, alternatively or in addition, possible to change the size of the field of view by advancing or retracting the X-ray imaging head in the YS direction. The field of view may be translated by adjusting the ZS and XS dimensions. Finally, the field of view may be reshaped by panning, or tilting, the X-ray imaging arrangement (BS, AS).

A field of view state comprising the aforementioned collimator and position settings is chosen by an operator, whilst illuminating the patient using the visible light source 48. Once satisfactory coverage of the region of interest has been provided, the X-ray source is activated, and the detector element 40 receives X-ray information about the region of interest 36. This is transmitted via data link 42 to the control arrangement 20. An operator may view the exposed X-ray image on an output device such as a monitor 44.

Thus, a conventional X-ray imaging system 18 has been described. It will be appreciated that the field of view may be controlled using automatic servomotor to set the collimator, or X-ray imaging source position, for example.

A specific challenge encountered in systems similar to that illustrated in FIG. 3 is in managing communication with a patient. There can be conflicting demands on an operator's attention, because the operator console 44 is often placed in a different room to the patient. Typically, the operator must move locations to inform the patient about movements that they should make to improve the image.

In general, this application alleviates the problems of communication with a patient. Firstly, it is proposed to annotate, on the system console (user interface) X-ray information to illustrate boundary errors using coloured indicators at peripheries of the displayed X-ray image data which are suffering a boundary error. This provides simple intuitive, and rapid feedback on the presence of FOV errors in the X-ray data.

It is also proposed to enhance the light-guide of an X-ray scanner, to enable detected FOV errors to be projected onto a region of interest of a patient. The operator can, thus, observe an FOV error and correct it without having to leave the patient alone in the imaging room.

According to a first aspect, there is provided a display unit 50 for an X-ray system. The display unit 50 comprises:
a data communication interface 52;
a processing unit 54; and
a display output unit 56.

The data communication interface 52 is configured to obtain first X-ray image data of a first portion of a region of interest of an object using an X-ray imager, wherein the first X-ray image data is obtained using an X-ray imager having an adjustable field of view set to an initial field of view state.

The processing unit 54 is configured to analyse the first X-ray image data to identify a boundary error in the first X-ray image data, to define a boundary error region contiguous to the first X-ray image data based on the analysis of the first X-ray image data; and to generate a boundary error indication based on the defined boundary error region.

The display output unit 56 is configured to display the boundary error indication to a user.

Therefore, it is possible to directly illustrate to a user 58 of an X-ray imager the fact that a further X-ray exposure will be required owing to an insufficient image quality. The omitted area can be clearly displayed to the user, either on a user interface (of the system console, for example), or on the region of interest of a patient, or both. This facilitates the re-setting of the field of view.

Typically, the data communication interface 52 comprises a LAN or WAN network connection, or a specific medical device communication standard interface such as PACS, for example. The data communication interface 52 enables first X-ray image data to be obtained from, for example, a detector element 40 of an X-ray acquisition system.

The processing unit 54 may optionally perform various pre-processing operations to format the first X-ray image data. The first X-ray image data, when formatted as an image, contains anatomical information such a rib cage boundary, lung boundaries, and the like. The processing unit is configured to analyse the first X-ray image data to identify a boundary error in the first X-ray image data. A boundary error is the result of the initial field of view state being incorrectly set for the first X-ray image acquisition. For example, an X-ray imaging source 34 could be angled inappropriately, or incorrectly collimated. A boundary error appears in the first X-ray image data as an unanatomical feature. For example, a cut-off view of the edge of a lung feature in the first X-ray image data would have, in the first X-ray image data, a smoothly contoured edge which would be interrupted abruptly at the edge of the field of view.

Such unanatomical features are optionally detectable using, for example, edge detection in the first X-ray image, and then applying a spline interpolation algorithm to the detected edge, or by monitoring the spatial rate of change along the detected edge. A detected rate of change along the edge which is greater than a pre-set threshold value indicates that an unanatomical feature is present.

Optionally, features detected within the field of view of the first X-ray image may be matched, even if the features in the first X-ray image data are incomplete owing to an error in the initial field of view state (caused, for example, by inappropriate collimation of the X-ray source).

This approach ensures a reliable and robust estimation of the field of view of the first X-ray image when provided with faulty images. An anatomical atlas approach allows an identification of the selected anatomy (such as the detection of lung field boundaries), or parts thereof, even when some elements of the anatomy which are being searched for are not present in the first X-ray image data.

Optionally, a comparison of the first X-ray image with an anatomical model (for example, a probabilistic atlas), enables deficiencies in the initial field of view state to be identified, and optionally for an improved proposed field of view to be defined. A probabilistic atlas may optionally be used as a reference coordinated system which encodes the complete field of view. Features in the first x-ray image data which are potentially partially missing can then be matched to elements within the probabilistic atlas. This approach ensures a reliable and robust estimation of the image field of view when provided with "cut-off" images, and enables comparison of the initial field of view state with an updated field of view state, used to re-set a collimator, for example.

Optionally, a second image acquisition using the updated field of view state enables acquisition of second X-ray information which partially incorporates, or exclusively comprises, the anatomical data missing from the first X-ray image data.

Therefore, a boundary error region at an edge of the first X-ray image can be derived based on the comparison of the first X-ray image data to an anatomical model. The boundary error region represents, for example, a part of the image in which, or next to which, useful anatomical information is lacking. For example, the boundary error region could define the location at which a lung lobe is cut-off within the first image data.

In an example, the boundary error region is provided by the processor fitting a rectangular "bounding box" around an area in the anatomical model or probabilistic atlas which is not robustly matched in the first X-ray image data. The coordinates of the bounding box may be transposed into the coordinates of the field of view. Updated field of view parameters may optionally then be generated from the coordinates of the bounding box, and used to alter a collimator setting of an X-ray source in a second x-ray exposure.

Following the detection of the boundary error region in the first X-ray image data, the boundary error region may be visualized by a display output unit 56.

In use, a patient is led into an X-ray imaging system similar to that illustrated in FIG. 2, but which additionally is equipped with the display unit 50. A first X-ray image exposure is made at an initial field of view setting and communicated to the display unit 50. Then, the display unit 50 analyses the first X-ray image data to identify a boundary error caused by an incorrect field of view setting in the X-ray imaging system, and determines a boundary error region. The display unit then displays the boundary error region either by displaying it on a user interface (system console) of the X-ray imaging system, by projecting it onto a portion of the region of interest of the patient, or both. This enables corrective action to be taken by the operator of the X-ray imaging system, and ensures that the patient does not leave the X-ray imaging system if an X-ray image with an incorrect field of view setting has been obtained.

Optionally, the display output unit further comprises:
a user interface display unit. The user interface display unit is further configured to display the boundary error indication on the user interface display unit.

Therefore, the boundary error region can be clearly displayed to a user on a screen of a digital X-ray machine, for example.

Optionally, the processing unit is further configured to combine the boundary error indication with the first X-ray image data to form annotated first X-ray image data, and the display output unit is further configured to display the boundary error indication to a user by displaying the annotated first X-ray image data on the user interface display unit.

The processing unit 54 is optionally further configured to generate, from the first X-ray image data and the coordinates of the boundary error region, output display image data which may be displayed on a user interface display unit, such as an LCD or OLED screen. The boundary error region is optionally displayed as a translucent overlay to the first X-ray image data, for example. Alternatively, the boundary error region is optionally displayed as a solid marker or cursor on the first X-ray image data, for example. Optionally, the boundary error region may be displayed as an alpha-numeric indication of what distance (in centimetres, for example) to the left or right of the image a collimator must be adjusted to include the full anatomy of interest.

In an alternative or additional embodiment of the display output unit 56, the boundary error region is projected onto the region of interest of a patient, whilst they are still standing in the field of view of the X-ray imaging system. Ideally, the patient will remain in the same position during an imaging process. The projection may be performed with a LCD projector, or through a colour-filter shutter arrangement, for example.

Optionally, 1D coloured lines may be projected onto a region of interest of a patient at the boundary of the field of view. The absence of a boundary error is signified using a first colour, such as green, and the presence of a boundary error is signified with a second colour, such as red.

Figure 4:
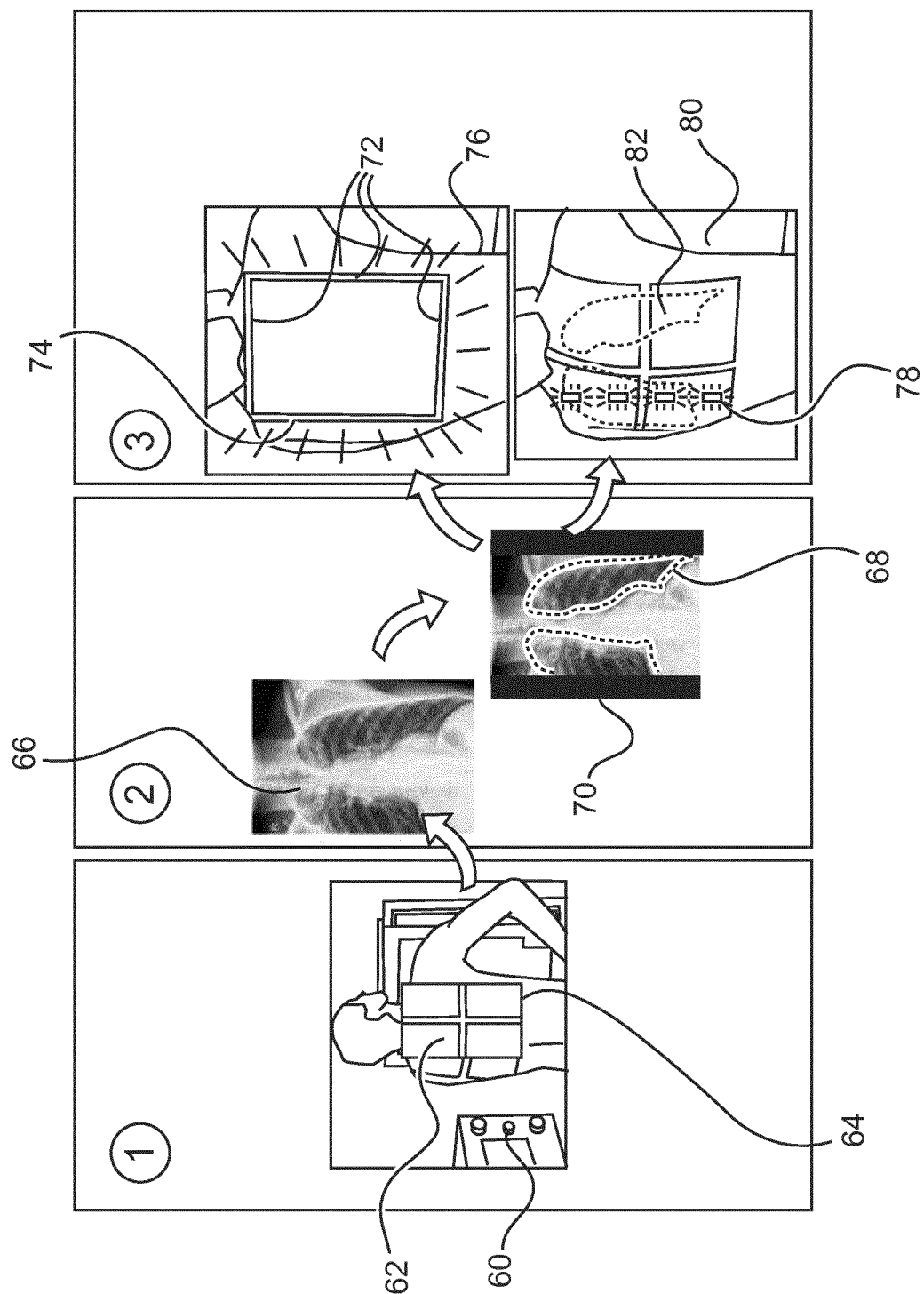
FIG. 4 illustrates an X-ray collimation process.

FIG. 4 shows a patient 64 standing in the field of interest of an X-ray scanning system. A collimation pattern 62 set by a collimation controller 60 is projected onto the back of the patient 64. Following the acquisition of first X-ray image data 66, the processing unit detects the presence of a boundary error as shown at image 68. In particular, the boundary error region 70 may be defined.

In a first output configuration shown at image 76, three lines are projected having a first colour (green, for example) onto the region of interest (back of the patient) on edges of the field of view which do not coincide with a boundary error. One line 74 having a second colour (red, for example) is projected onto the region which coincides with a boundary error.

In a second output configuration, shown at image 80, only one line 78 is projected onto a region of interest coinciding with a boundary error when the initial view state has been used.

In a third output configuration, a trace of the patient's anatomy 82, as extracted from the first X-ray image data and matched to an anatomical atlas, is projected onto the region of interest of the patient. In combination with the first or second configurations, or alone, it can clearly be seen that the anatomy has been subject to a field of view setting error. It will be appreciated that the projection of a trace of the patient's anatomy is preferably performed using a digital projector such as an LCD projector, but that the projection of the lines 72, 74, 78 could be achieved using a digital projection means such as an LCD projector, or "analogue" means such as a movable colour filter in front of a light source.

Optionally, the processing unit 54 is configured to combine the first X-ray image data with the boundary error region to form annotated X-ray information. The annotated X-ray information may be communicated by the processing unit 54 to a data retrieval system. Therefore, the annotated X-ray information may be incorporated into report generation approaches, to provide information on boundary errors in a patient's medical file, for example.

Optionally, the display unit further comprises:
a projection unit.

The display output unit is further configured to project the boundary error indication onto a second portion of the region of interest of the object using the projection unit.

Therefore, a boundary error region may be directly projected onto the region of interest of the patient in a way that is difficult for a system user to overlook. This reduces the likelihood that a user would leave the X-ray room before corrective action (such as the taking of a new X-ray image) is taken.

Optionally, the processing unit is further configured to calculate an updated field of view state, and to display the updated field of view indication by (i) projecting the updated field of view indication onto a third portion of the region of interest of the object, and/or (ii) displaying the updated field of view indication on the user interface display unit.

Optionally, the projection unit comprises a digital projection unit. The boundary error indication is projected onto a second portion of the region of interest of the object using a digital projection unit.

Optionally, the processing unit is configured to generate contour mask data of the first X-ray image. Optionally, this is achieved by edge detecting and segmenting the first X-ray image data. The contour mask data is projected onto the region of interest using the digital projection unit. Optionally, the contour mask data includes the boundary error indication.

Therefore, a digital projection unit may provide indications of boundary error regions having many different shapes, optionally referenced to the patient's anatomy.

Optionally, the projection unit further comprises:
a light filter element operatively coupled to the processing unit and configurable to extend at least partially over the periphery of a light path of a light source directed at the region of interest.

The processing unit is further configured to actuate the light filter element to extend at least partially over the periphery of the light path of the light source located inside the X-ray source based on the boundary error indication, and to send an illumination signal to illuminate a light source inside the X-ray source.

Therefore, the existing light illumination mechanism of many X-ray machines may be adapted to highlight peripheral errors in the setting of the field of view.

Figure 5:
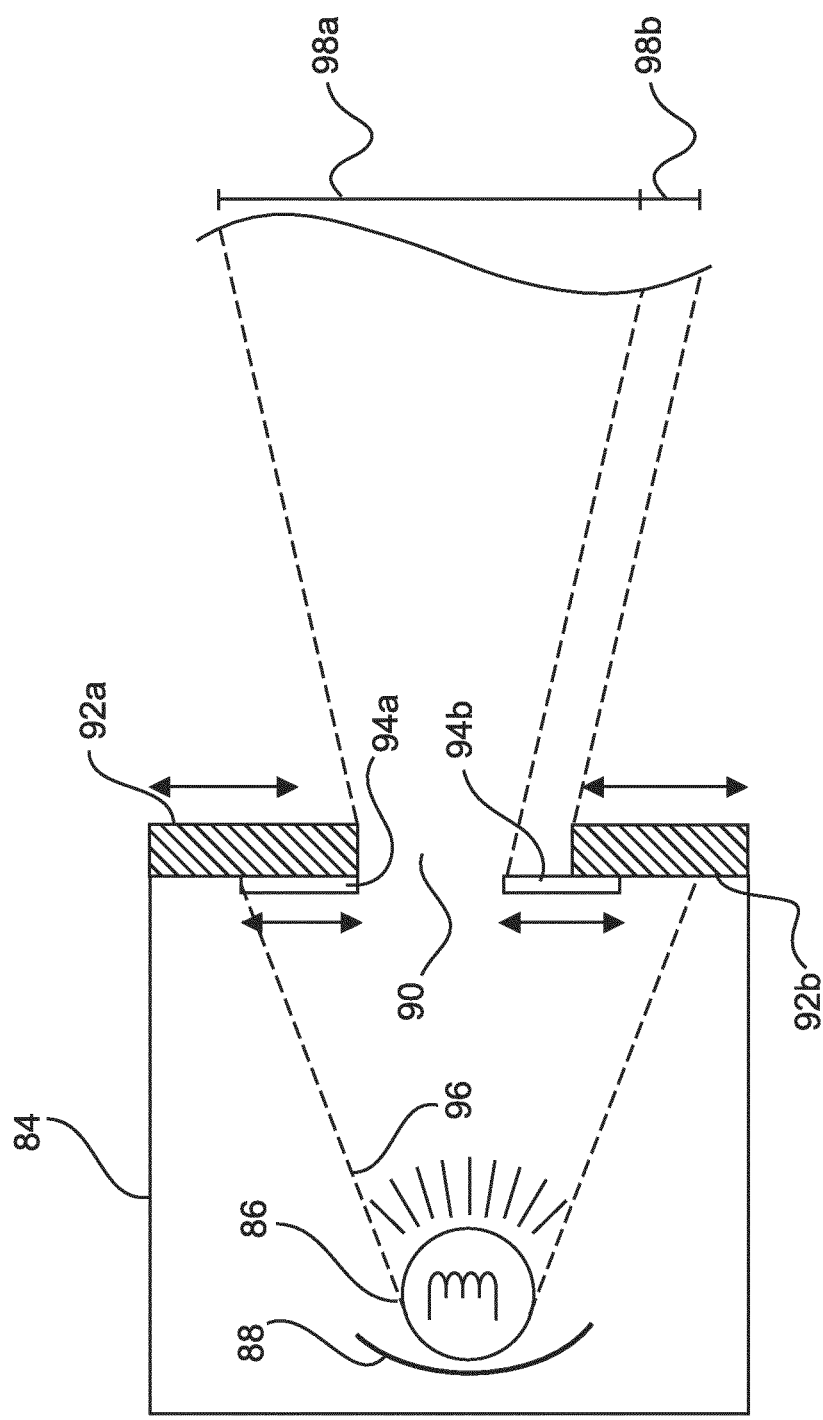
FIG. 5 illustrates a schematic view of a display unit using light filters.
Figure 6:
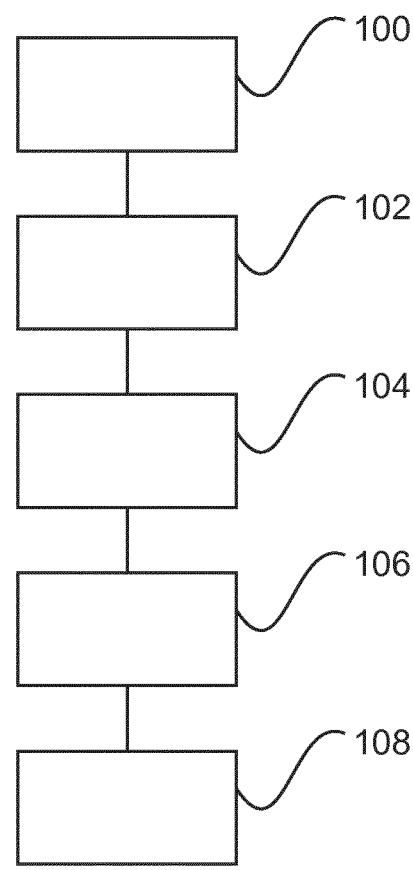
FIG. 6 illustrates a method in accordance with a third aspect.

FIG. 5 illustrates an X-ray source arranged to generate display indicia. The enclosure 84 of the X-ray source comprises a light source 86, an aperture 90 and optionally a reflector 88 such that the X-ray source enclosure functions as a "light box". For simplicity, FIG. 5 does not show the X-ray source, but the box would also contain a rotating anode X-ray tube, for example, arranged to emit X-ray radiation towards the aperture 90. The aperture of the box is defined by a plurality of high-density (molybdenum, for example) movable shutters 92a and 92b, which can be set by actuation means (not shown) to collimate a beam of X-rays or visible light leaving the X-ray source. Visible light filter means 94a and 94b (such as filtered glass, or a filter gel material) are arranged to be actuated, respectively, extending into the light beam 96. The actuation is based on a signal derived from the boundary error region information calculated by the processing means. Therefore, a region having the natural colour of the light source 86 will be projected onto a region of interest at portion 98a, and a region having the colour of the visible light filter means will be projected onto the region of interest at portion 98b.

Optionally, the boundary error indication and/or the updated field of view indication is displayed on the user interface and/or on a portion of the region of interest of the object using one or more of (i) a coloured rectangular indication, (ii) a region having lower or higher brightness compared to the first and/or second X-ray image data, (iii) a flashing indication, (iv) an outline of an anatomical feature optionally comprising an indication of a cut-off region.

Optionally, the processing unit is configured to analyse the first X-ray image data by comparing a portion of the first X-ray image data to an anatomical model and/or a probabilistic anatomical atlas.

According to a second aspect, there is provided an X-ray imaging system comprising:
an X-ray source;
an X-ray detector; and
a display unit according to the first aspect or its optional embodiments.

The X-ray source is configured in an initial field of view state to illuminate a region of interest of an object with X-ray radiation, and the X-ray detector is configured to receive first X-ray image data of a first portion of the region of interest of an object.

The display unit is configured to display a boundary error indication of the first X-ray image data to a user.

According to a third aspect, a method for identifying a boundary error in X-ray image data is provided. The method comprises:
a) obtaining 100 first X-ray image data of a first portion of a region of interest of an object using an X-ray imager, wherein the first X-ray image data is obtained using an X-ray imager having an adjustable field of view set to an initial field of view state;
b) analysing 102 the first X-ray image data to identify a boundary error in the first X-ray image data;
c) defining 104 a boundary error region contiguous to the first X-ray image data based on the analysis of the first X-ray image data;
d) generating 106 a boundary error indication based on the boundary error region; and
e) displaying 108 to a user the boundary error indication.

Optionally, displaying the boundary error indication to a user further comprises:
e1) displaying the boundary error indication on a user interface display of an X-ray imaging system.

Optionally, the method further comprises:
e2) combining the boundary error indication with the first X-ray image data to form annotated first X-ray image data, and
e3) wherein displaying the boundary error indication to a user further comprises: displaying the annotated first X-ray image data on a user interface display.

Optionally, displaying the boundary error indication to a user further comprises:
e4) projecting the boundary error indication onto a second portion of the region of interest of the object.

Optionally projecting the boundary error indication onto a second portion of the region of interest of the object further comprises:
e5) configuring a light filter element to extend into a light path of a light source located inside the X-ray source based on the boundary error indication; and
e6) illuminating the light source inside the X-ray source.

Optionally, the boundary error indication is projected onto a second portion of the region of interest of the object using a digital projection unit.

Optionally, the method further comprises:
f) calculating an updated field of view state; and
g) displaying an updated field of view indication;
wherein the updated field of view indication is projected onto a third portion of the region of interest of the object, and/or displayed on the user interface display of an X-ray imaging system.

Optionally, the method further comprises:
h) receiving from the user a command to acquire a second X-ray image;
i) adjusting the field of view of the X-ray imager to an updated field of view state; and
j) acquiring second X-ray image data at the adjusted field of view state.

Optionally, the method further comprises:

wherein in step b), the analysis of the first X-ray image data comprises comparing the first X-ray image data to an anatomical model.

According to a fourth aspect there is provided a computer program element for controlling the display unit according to the first aspect or its embodiments, which, when the computer program element is executed by a processing unit, is adapted to perform the method of the third aspect.

According to a fifth aspect of the invention, there is provided a computer-readable medium having stored the computer program element of the fourth aspect.

A computer program element might therefore be stored on a computer unit, which might also be part of an embodiment of the present invention. This computing unit may be adapted to perform or induce performance of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention. A computer program may be stored and/or distributed on a suitable medium, such as an optical storage media or a solid state medium supplied together with, or as a part of other hardware, but may also be distributed in other forms, such as via the Internet or other wired or wireless telecommunication systems.

However, the program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should be to be noted that embodiments of the invention are described with reference to different subject-matters. In particular, some embodiments are described with reference to method-type claims, whereas other embodiments are described with reference to the device-type claims. However, a person skilled in the art will gather from the above, and the following description, that unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A display for an X-ray system, comprising:
    a data communication interface configured to obtain X-ray image data of a first portion of a region of interest of an object using an X-ray imaging source assembly, wherein the X-ray image data is obtained using the X-ray imaging source assembly having an adjustable field of view set to an initial field of view state;
    a processor configured to:
        identify a boundary error in the X-ray image data;
        based on the boundary error, define a boundary error region contiguous to the X-ray image data;
        generate a boundary error indication based on the defined boundary error region; and
    project the boundary error indication onto a second portion of the region of interest of the object.

2. The display according to claim 1, further comprising a user interface display configured to display the boundary error indication.

3. The display according to claim 2, wherein the processor is further configured to calculate an updated field of view, wherein the updated field of view is projected onto a third portion of the region of interest of the object, and/or wherein the updated field of view is displayed on the user interface display.

4. The display according to claim 2,
    wherein the processor is further configured to combine the boundary error indication with the X-ray image data to form annotated X-ray image data such that the annotated X-ray image data is displayed on the user interface display.

5. The display according to claim 3, wherein the boundary error indication and/or the updated field of view indication is displayed on the user interface and/or on a portion of the region of interest of the object using at least one of 1) a coloured rectangular indication, 2) a region having lower or higher brightness compared to the X-ray image data, 3) a flashing indication, and 4) an outline of an anatomical feature.

6. The display according to claim 1, further comprising a light filter operatively coupled to the processor, wherein the processor is further configured to configure the light filter to extend at least partially over the periphery of the light path of the light source located inside the X-ray imaging source assembly based on the boundary error indication, and to send an illumination signal to illuminate the light source inside the X-ray imaging source assembly.

7. The display according to claim 1, wherein the processor is configured to analyze the X-ray image data by comparing the X-ray image data to an anatomical model and/or a probabilistic anatomical atlas.

8. A method for identifying a boundary error in X-ray image data, comprising:
    obtaining the X-ray image data of a first portion of a region of interest of an object using an X-ray imaging source assembly, wherein the X-ray image data is obtained using the X-ray imaging source assembly having an adjustable field of view set to an initial field of view state;
    analyzing the X-ray image data to identify a boundary error in the X-ray image data;

defining a boundary error region contiguous to the X-ray image data based on the boundary error;
generating a boundary error indication based on the boundary error region;
displaying the boundary error indication; and
projecting the boundary error indication onto a second portion of the region of interest of the object.

9. The method according to claim 8, further comprising:
combining the boundary error indication with the X-ray image data to form annotated X-ray image data; and
displaying the annotated X-ray image data.

10. The method according to claim 8, further comprising:
calculating an updated field of view;
projecting the updated field of view onto a third portion of the region of interest of the object; and
displaying the updated field of view.

11. The method according to claim 8, further comprising:
providing a light filter;
configuring the light filter to extend at least partially over the periphery of the light path of the light source located inside an X-ray source based on the boundary error indication; and
sending an illumination signal to illuminate the light source inside the X-ray source.

12. The method according to claim 8, further comprising analyzing the X-ray image data by comparing the X-ray image data to an anatomical model and/or a probabilistic anatomical atlas.

13. A non-transitory computer-readable medium having one or more executable instructions stored thereon, which, when executed by a processor, cause the processor to perform a method for identifying a boundary error in X-ray image data, the method comprising:
obtaining the X-ray image data of a first portion of a region of interest of an object using an X-ray imaging source assembly, wherein the X-ray image data is obtained using the X-ray imaging source assembly having an adjustable field of view set to an initial field of view state;
analyzing the X-ray image data to identify a boundary error in the X-ray image data;
defining a boundary error region contiguous to the X-ray image data based on the boundary error;
generating a boundary error indication based on the boundary error region;
displaying the boundary error indication; and
projecting the boundary error indication onto a second portion of the region of interest of the object.

* * * * *